United States Patent
Old et al.

(10) Patent No.: US 9,090,584 B2
(45) Date of Patent: Jul. 28, 2015

(54) THERAPEUTIC AGENTS FOR TREATMENT OF OCULAR HYPERTENSION

(75) Inventors: David W. Old, Irvine, CA (US); Todd Gac, Santa Ana, CA (US)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 13/011,370

(22) Filed: Jan. 21, 2011

(65) Prior Publication Data

US 2011/0184055 A1 Jul. 28, 2011

Related U.S. Application Data

(60) Provisional application No. 61/298,428, filed on Jan. 26, 2010.

(51) Int. Cl.
*A61K 31/381* (2006.01)
*C07D 333/40* (2006.01)
*A61P 27/06* (2006.01)

(52) U.S. Cl.
CPC ............ *C07D 333/40* (2013.01); *A61K 31/381* (2013.01)

(58) Field of Classification Search
USPC .......................................... 514/448; 549/71
See application file for complete search history.

(56) References Cited

U.S. PATENT DOCUMENTS

| 4,166,452 A | 9/1979 | Generales |
| 4,256,108 A | 3/1981 | Theeuwes |
| 4,265,874 A | 5/1981 | Bonsen |
| 5,739,141 A | 4/1998 | Varney |
| 5,824,691 A | 10/1998 | Kuno |
| 7,091,231 B2 | 8/2006 | Donde |
| 7,427,685 B2 | 9/2008 | Donde |
| 2004/0072871 A1* | 4/2004 | Dublanchet et al. .......... 514/336 |

FOREIGN PATENT DOCUMENTS

| WO | WO 98-028264 | 7/1998 |
| WO | WO 2006-062224 | 6/2006 |
| WO | WO 2008-094958 | 8/2008 |

OTHER PUBLICATIONS

Vippagunta et al., Crystalline solids, 2001, Advanced Drug Delivery Reviews, 48, pp. 3 and 18.*
Goldberg et al., Synthesis of the 2-omega-Aminoalkyl and 2-omega-Sulphanilamidoalkyl Derivatives of Thiazole and Pyrimidine, 1947, Journal of the Chemical Society, 1372-1377.*
Lapina et al., Reactions of Alkyl (Halomethyl)furancarboxylates with Hexamethylenetetramine, 2006, Russian Journal of General Chemistry, vol. 76, No. 8, 1304-1309.*
Remington's Pharmaceutical Sciences, 16th Edition, 1980.
Thomas Ruckle, Design, Synthesis, and Biogical Activity of Novel, Potent, and Selective (Benzoylaminomethyl)thiophene Sulfonamide Inhibitors of C-Jun-N-Terminal Kinase, J. Med. Chem., 2004, 47, 6921-6934.

* cited by examiner

*Primary Examiner* — Kristin Vajda
(74) *Attorney, Agent, or Firm* — Jonathan Y. Bass

(57) ABSTRACT

The invention provides well-defined amides for treating glaucoma and ocular hypertension.

24 Claims, No Drawings

THERAPEUTIC AGENTS FOR TREATMENT OF OCULAR HYPERTENSION

RELATED APPLICATION

This application claims the benefit of U.S. Provisional Application Ser. No. 61/298,428, filed Jan. 26, 2010, the disclosure of which is hereby incorporated in its entirety herein by reference.

FIELD OF THE INVENTION

The present invention relates generally to compounds and methods for treating ocular disorders. The invention relates specifically to the use of certain well-defined amides for the treatment of ocular hypertension and glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

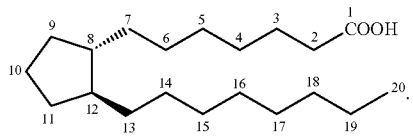

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by a or β [e.g. prostaglandin $F_{2\alpha}$ ($PGF_{2\beta}$)].

SUMMARY OF THE INVENTION

The invention provides well-defined amides for treating glaucoma and ocular hypertension. In one embodiment of the invention, there are provided compounds having the structure:

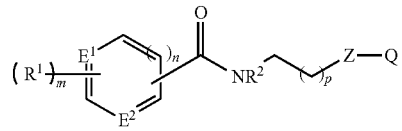

wherein:
$E^1$ and $E^2$ are each independently $CR^1$, O, NH, N or S;
Q is $CO_2R^3$, $CH_2OR^3$, $CON(R^3)_2$, or tetrazol-5-yl;
Z is interarylene, n-propyl, $CH_2SCH_2$, or $CH_2OCH_2$;
each $R^1$ is independently H, alkyl, halogen, $CF_3$, alkoxy, substituted $C_5$-$C_7$ aryl, $C_5$-$C_7$ arylalkyl;
$R^2$ is H or lower alkyl;
$R^3$ is H, lower alkyl, phenyl, biphenyl, —$CH_2CH_2OH$, $CF_3$, $C(O)R^3$, or $SO_2R^3$;
n is 0 or 1;
m is 0 to 5, with the proviso that when m is 0, at least one of $E^1$ and $E^2$ is $CR^1$; and
p is 0 to 5;
or pharmaceutically acceptable salts, hydrates, solvates, and crystal forms, isomers, tautomers, enantiomers, and diastereomers thereof.

In another embodiment of the invention, there are provided compositions including at least one compound of the invention, wherein the composition is a liquid which is ophthalmically acceptable.

In another embodiment of the invention there are provided methods for treating glaucoma or ocular hypertension. Such methods can be performed, for example, by administering to a subject in need thereof a compound of the invention.

In still another embodiment of the invention, there are provided kits including at least one composition of the invention, a container, and instructions for administration of the composition to a subject in need thereof for the treatment of glaucoma or ocular hypertension.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —$CH_2$O$R_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

As used herein "interarylene" refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

As used herein tetrazol-5-yl refers to a moiety having the tautomeric forms depicted below:

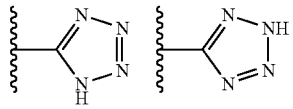

The two tautomeric forms rapidly interconvert in aqueous or biological media and are thus equivalent to one another.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

The invention provides well-defined compounds having the structure:

$$(R^1)_m \underset{E^2}{\overset{E^1}{\diagdown}} \diagup_n \overset{O}{\underset{}{C}} NR^2 (\quad)_p Z-Q$$

wherein:

$E^1$ and $E^2$ are each independently $CR^1$, O, NH, N or S;

Q is $CO_2R^3$, $CH_2OR^3$, $CON(R^3)_2$, or tetrazol-5-yl;

Z is interarylene, n-propyl, $CH_2SCH_2$, or $CH_2OCH_2$;

each $R^1$ is independently H, alkyl, halogen, $CF_3$, alkoxy, substituted $C_5$-$C_7$ aryl, $C_5$-$C_7$ arylalkyl;

$R^2$ is H or lower alkyl;

$R^3$ is H, lower alkyl, phenyl, biphenyl, —$CH_2CH_2OH$, $CF_3$, $C(O)R^3$, or $SO_2R^3$;

n is 0 or 1;

m is 0 to 5, with the proviso that when m is 0, at least one of $E^1$ and $E^2$ is $CR^1$; and p is 0 to 5;

or pharmaceutically acceptable salts, hydrates, solvates, and crystal forms, isomers, tautomers, enantiomers, and diastereomers thereof.

In some embodiments of the invention, the interarylene is substituted or unsubstituted interphenylene, interthiophenylene, interfurylene, interpyridinylene, interoxazolylene, and interthiazolene. In certain embodiments of the invention, the interarylene is interthiophenylene. In other embodiments the interarylene is furylene and interthiazolene.

The compounds of the invention may contain a wide a variety of substituents. When invention compounds bear substituents, the substituents are typically selected from alkyl, alkenyl, alkynyl, hydroxy, alkoxy, heterocyclic, aryl, heteroaryl, aryloxy, halogen, haloalkyl, cyano, nitro, amino, lower alkylamino, lower dialkylamino, amido, azido, acyl (—C(O)$R_6$), alkoxymethyl, mercapto (—S—$R_6$), sulfoxy (—S(O)—$R_6$), sulfonyl (—S(O)$_2$—$R_6$), sulfonamide (—S(O)$_2$N($R_6$)$_2$), carbonate (—OC(O)—O—$R_6$), oxyacyl (—OC(O)—$R_6$), carboxyl (—C(O)OH), ester (—C(O)O$R_6$), carbamate (—OC(O)—N($R_6$)$_2$), wherein $R_6$ is H or lower alkyl, lower alkenyl, lower alkynyl, aryl, heteroaryl, heterocycle, and the like.

In some embodiments, $R^1$ is substituted $C_5$-$C_7$ aryl. In certain embodiments $R^1$ is substituted phenyl bearing substituents such as, for example, halogen, lower alkyl, lower alkoxy, or $CF_3$. In some embodiments the substituent is halogen. In certain embodiments the substituent is fluoro.

In other embodiments of the invention, Q is $CO_2R^3$. In some embodiments $R^3$ is H or lower alkyl. In certain embodiments $R^3$ is H.

Exemplary compounds contemplated for use in the practice of the invention include, but are not limited to, compounds having any one of the following structures:

Compound 1

Compound 2

Compound 3

Compound 4

Compound 5

Compound 6

Compound 7

The compounds of the invention can be prepared in a variety of ways well known to those skilled in the art. Scheme A set forth below outlines an exemplary synthetic route to the compounds of the invention.

Scheme A

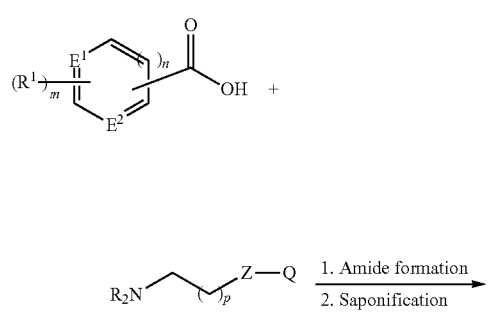

1. Amide formation
2. Saponification

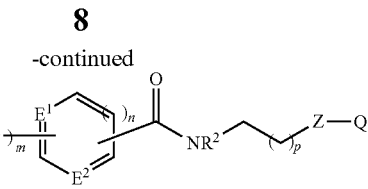

Data from running binding and activity studies on the compounds of the invention were carried out as described in U.S. Pat. No. 7,427,685, the contents of which are incorporated herein by reference. The results set forth below in Table 1 demonstrate that the compounds disclosed herein are selective prostaglandin $EP_2$ agonists, and are thus useful for the treatment of glaucoma, ocular hypertension, inflammatory bowel disease, and the other diseases or conditions disclosed herein.

TABLE 1

| Structure | EP2 data | | | EP4 data | | Other Receptors (EC50 in nM) | | | | | |
| | flipr EC50 | cAMP EC50 | Ki | flipr EC50 | KI | hFP | hEP1 | hEP3A | hTP | hIP | hDP |
| --- | --- | --- | --- | --- | --- | --- | --- | --- | --- | --- | --- |
| Compound 1 | 49 | 2 | 63 | 5142 | 648 | NA | NA | 8897 | NA | NA | NA |
| Compound 2 | >10000 | >10000 | 631 | >10000 | 845 | NA | NA | NA | NA | NA | NA |
| Compound 3 | 31 | 5 | 177 | >10000 | 1477 | NA | NA | 3286 | NA | NA | NA |
| Compound 4 | >10000 | >10000 | 6879 | >10000 | 8638 | NA | NA | NA | NA | NA | NA |
| Compound 5 | 26 | 8 | 150 | 6024 | 739 | NA | NA | >10,000 | NA | NA | NA |
| Compound 6 | 11 | 4 | 122 | 4436 | 750 | NA | NA | 4815 | NA | NA | NA |

TABLE 1-continued

| | EP2 data | | | EP4 data | | Other Receptors (EC50 in nM) | | | | | |
| | flipr | cAMP | | flipr | | | | | | | |
| Structure | EC50 | EC50 | Ki | EC50 | KI | hFP | hEP1 | hEP3A | hTP | hIP | hDP |
|---|---|---|---|---|---|---|---|---|---|---|---|
| 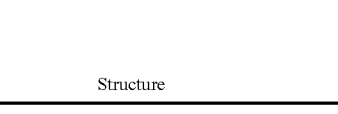 Compound 7 | 37 | 5 | 126 | >10000 | 814 | NA | NA | 1424 | NA | NA | NA |

Those skilled in the art will readily understand that for administration or the manufacture of medicaments the compounds disclosed herein can be admixed with pharmaceutically acceptable excipients which per se are well known in the art. Specifically, a drug to be administered systemically, it may be connected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;
Adrenergic Agonists including
non-selective adrenergic agonists such as epinephrine borate, epinephrine hydrochloride, and dipivefrin, and the like, or pharmaceutically acceptable salts or prodrugs thereof; and
$\alpha_2$-selective adrenergic agonists such as apraclonidine, brimonidine, and the like, or pharmaceutically acceptable salts or prodrugs thereof;
Carbonic Anhydrase Inhibitors including acetazolamide, dichlorphenamide, methazolamide, brinzolamide, dorzolamide, and the like, or pharmaceutically acceptable salts or prodrugs thereof;
Cholinergic Agonists including
direct acting cholinergic agonists such as carbachol, pilocarpine hydrochloride, pilocarbine nitrate, pilocarpine, and the like, or pharmaceutically acceptable salts or prodrugs thereof;
chlolinesterase inhibitors such as demecarium, echothiophate, physostigmine, and the like, or pharmaceutically acceptable salts or prodrugs thereof;
Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifcdimpinc, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and
Prostaglandins including travoprost, UFO-21, chloprostenol, fluprostenol, 13,14-dihydro-chloprostenol, isopropyl unoprostone, latanoprost and the like.
Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

The following examples are intended only to illustrate the invention and should in no way be construed as limiting the invention.

EXAMPLES

Example 1

5-(2-(3',4-Difluoro-[1,1'-biphenyl]-3-ylcarboxamido)ethyl)thiophene-2-carboxylic acid Step 1. 3',4-Difluoro-[1,1'-biphenyl]-3-carboxylic acid A 50 mL Schlenk tube was charged with (3-fluorophenyl)boronic acid (140 mg, 1.0 mmol), 5-bromo-2-fluorobenzoic acid (263 mg, 1.2 mmol), tetrakis(triphenylphosphine)palladium (0) (58 mg, 0.05 mmol) and cesium carbonate (1.3 g, 4.0 mmol). Ethanol (5 mL) and toluene (5 mL) were added and the tube was sealed and heated at 80° C. for 3 h. The cooled mixture was transferred to a flask, washing with ethanol, and concentrated in vacuo. The residue was diluted with water (10 mL) and extracted with EtOAc (2×10 mL). The aqueous phase was acidified with 1.0 N aqueous HCl (10 mL) and extracted with EtOAc (3×10 mL). The extracts were dried ($Na_2SO_4$), filtered and concentrated in vacuo. $^1$H-NMR showed the desired product, 3',4-difluoro-[1,1'-biphenyl]-3-carboxylic acid, was slightly contaminated with 2-fluorobenzoic acid. The impure product (215 mg, ~92%) was used without further purification.

Step 2. Isopropyl 5-(2-(3',4-difluoro-[1,1'-biphenyl]-3-ylcarboxamido)ethyl)thiophene-2-carboxylate 1-Ethyl-3-(3'dimethylaminopropyl)-carbodiimide hydrochloride (EDCI, 204 mg, 1.06 mmol) was added to a solution of the impure acid from step 1 (192 mg, 0.82 mmol) and isopropyl 5-(2-aminoethyl)thiophene-2-carboxylate from preparation 1 (175 mg, 0.82 mmol) in $CH_2Cl_2$ (8.2 mL) and the solution was stirred at room temperature overnight. The reaction was concentrated in vacuo, diluted with water (25 mL) and extracted with EtOAc (3×25 mL). The extracts were dried ($Na_2SO_4$), filtered (washing with excess EtOAc) and concentrated in vacuo. The crude residue was purified on 40 g silica (100% hexanes→100% EtOAc, gradient) to afford 115 mg (33%) of isopropyl 5-(2-(3',4-difluoro-[1,1'-biphenyl]-3-ylcarboxamido)ethyl)thiophene-2-carboxylate.

Step 3. 5-(2-(3',4-Difluoro-[1,1'-biphenyl]-3-ylcarboxamido)ethyl)thiophene-2-carboxylic acid Aqueous 1 N lithium hydroxide (0.92 mL, 0.92 mmol) was added to a solution of the ester from step 2 (79 mg, 0.18 mmol) in THF (0.92 mL) in a scintillation vial. The vial was sealed and heated at 60° C. After 3 d, the reaction mixture was allowed to cool and the volatiles were evaporated under a stream of nitrogen. The residue was diluted with water (1.0 mL), acidified with 1 N aqueous HCl (2.0 mL), and extracted with EtOAc (3×10 mL). The combined extracts were dried (Na$_2$SO$_4$), filtered and concentrated in vacuo to afford 71 mg (99%) of the title compound as a tan solid.

Example 2

5-((3',4-Difluoro-[1,1'-biphenyl]-3-ylcarboxamido) methyl)thiophene-2-carboxylic acid Step 1. Methyl 5-((3',4-difluoro-[1,1'-biphenyl]-3-ylcarboxamido)methyl)thiophene-2-carboxylate In accordance with the procedure of Example 1, step 2, the impure acid from Example 1, step 1 (117 mg, 0.50 mmol) and methyl 5-(aminomethyl)thiophene-2-carboxylate (see *J. Med. Chem.* 2004, 47, 6921-6934; 86 mg, 0.50 mmol) were converted into 60 mg (31%) of methyl 5-((3',4-difluoro-[1,1'-biphenyl]-3-ylcarboxamido)methyl)thiophene-2-carboxylate.

Step 2. 5-((3',4-Difluoro-[1,1'-biphenyl]-3-ylcarboxamido)methyl)thiophene-2-carboxylic acid Aqueous 1 N lithium hydroxide (0.2 mL, 0.2 mmol) was added to a solution of the ester from step 1 (15.5 mg, 0.04 mmol) in THF (0.2 mL) in a 1 dram vial. The vial was sealed and heated at 40° C. After 18 h, the reaction mixture was allowed to cool and the volatiles were evaporated under a stream of nitrogen. The residue was diluted with water (1.0 mL), acidified with 1 N aqueous HCl (0.5 mL), and extracted with EtOAc (3×2 mL). The combined extracts were washed with brine (2 mL), dried (Na$_2$SO$_4$), filtered (washing with excess EtOAc) and concentrated in vacuo to afford 15 mg (quant.) of the title compound as a colorless solid.

Example 3

5-(3-(3',4-Difluoro-[1,1'-biphenyl]-3-ylcarboxamido) propyl)thiophene-2-carboxylic acid Step 1. Methyl 5-(3-(5-bromo-2-fluorobenzamido) propyl)thiophene-2-carboxylate In accordance with the procedure of Example 1, step 2, methyl 5-(3-aminopropyl)thiophene-2-carboxylate (see WO98/028264; 107 mg, 0.54 mmol) and 5-bromo-2-fluorobenzoic acid (100 mg, 0.46 mmol) were converted into 40 mg (22%) methyl 5-(3-(5-bromo-2-fluorobenzamido)propyl)thiophene-2-carboxylate.

Step 2. 5-(3-(3',4-Difluoro-[1,1'-biphenyl]-3-ylcarboxamido)propyl)thiophene-2-carboxylic acid In accordance with the procedure of Example 1, step 1, the aryl bromide from step 1 (40 mg, 0.10 mmol) and (3-fluorophenyl)boronic acid (15 mg, 0.11 mmol), were converted into 20 mg (50%) of the title compound after purification employing 3% AcOH/EtOAc.

Example 4

5-(4-(3',4-Difluoro-[1,1'-biphenyl]-3-ylcarboxamido) butyl)thiophene-2-carboxylic acid Step 1. Methyl 5-(4-(5-bromo-2-fluorobenzamido) butyl)thiophene-2-carboxylate In accordance with the procedure of Example 1, step 2, methyl 5-(4-aminobutyl)thiophene-2-carboxylate (see US 2008/0119539; 113 mg, 0.50 mmol) and 5-bromo-2-fluorobenzoic acid (100 mg, 0.46 mmol) were converted into 85 mg (45%) of methyl 5-(4-(5-bromo-2-fluorobenzamido)butyl)thiophene-2-carboxylate.

Step 2. 5-(4-(3',4-Difluoro-[1,1'-biphenyl]-3-ylcarboxamido)butyl)thiophene-2-carboxylic acid In accordance with the procedure of Example 1, step 1, the aryl bromide from step 1 (85 mg, 0.21 mmol) and (3-fluorophenyl)boronic acid (100 mg, 0.11 mmol), were converted into 15 mg (18%) of the title compound after purification employing 3% AcOH/EtOAc.

Example 5

5-(2-(3'-Fluoro-[1,1'-biphenyl]-3-ylcarboxamido) ethyl)thiophene-2-carboxylic acid Step 1. Isopropyl 5-(2-(3'-fluoro-[1,1'-biphenyl]-3-ylcarboxamido)ethyl)thiophene-2-carboxylate In accordance with the procedure of Example 1, step 2,3'-fluoro-[1,1'-biphenyl]-3-carboxylic acid (see U.S. Pat. No. 5,824,691; 43 mg, 0.20 mmol) and isopropyl 5-(2-aminoethyl)thiophene-2-carboxylate (43 mg, 0.20 mmol) were converted into 75 mg (91%) of isopropyl 5-(2-(3'-fluoro-[1,1'-biphenyl]-3-ylcarboxamido)ethyl)thiophene-2-carboxylate.

Step 2. 5-(2-(3'-Fluoro-[1,1'-biphenyl]-3-ylcarboxamido)ethyl)thiophene-2-carboxylic acid In accordance with the procedure of Example 1, step 3, the ester from step 1 (15 mg, 0.036 mmol) was converted into 12 mg (89%) of the title compound.

Example 6

5-(2-(3',5-Difluoro-[1,1'-biphenyl]-3-ylcarboxamido) ethyl)thiophene-2-carboxylic acid Step 1. 3',5-Difluoro-[1,1'-biphenyl]-3-carboxylic acid A 2 dram vial was charged with (3-fluorophenyl)boronic acid (168 mg, 1.2 mmol), 3-chloro-5-fluorobenzoic acid (175 mg, 1.0 mmol), potassium carbonate (345 mg, 2.5 mmol), palladium acetate (1.1 mg, 0.005 mmol) and 2-dicyclohexylphosphino-2,6-dimethoxy-3-sulfonato-1,1'-biphenyl hydrate sodium salt (5 mg, 0.01 mmol). The vial was fitted with a septum cap, degassed water (1.5 mL) was added and the mixture was purged with nitrogen and stirred at room temperature. After stirring for 4 d, the mixture was diluted with water (30 mL), acidified to pH 4 with 1.0 N aqueous HCl and extracted with EtOAc (3×25 mL). The combined extracts were dried (Na$_2$SO$_4$), filtered and concentrated in vacuo to afford 235 mg (quant.) of 3',5-difluoro-[1,1'-biphenyl]-3-carboxylic acid which was used without further purification.

Step 2. Isopropyl 5-(2-(3',5-difluoro-[1,1'-biphenyl]-3-ylcarboxamido)ethyl)thiophene-2-carboxylate In accordance with the procedure of Example 1, step 2, the acid from step 1 (47 mg, 0.20 mmol) and isopropyl 5-(2-aminoethyl)thiophene-2-carboxylate (43 mg, 0.20 mmol)

were converted into 74 mg (86%) of isopropyl 5-(2-(3',5-difluoro-[1,1'-biphenyl]-3-ylcarboxamido)ethyl)thiophene-2-carboxylate.

Step 3. 5-(2-(3',5-Difluoro-[1,1'-biphenyl]-3-ylcarboxamido)ethyl)thiophene-2-carboxylic acid In accordance with the procedure of Example 1, step 3, the ester from step 1 (15 mg, 0.035 mmol) was converted into 12 mg (89%) of the title compound.

Example 7

5-(3-(3',5-Difluoro-[1,1'-biphenyl]-3-ylcarboxamido)propyl)thiophene-2-carboxylic acid Step 1. Methyl 5-(2-(3-bromo-5-fluorobenzamido)ethyl)thiophene-2-carboxylate In accordance with the procedure of Example 1, step 2, methyl 5-(3-aminopropyl)thiophene-2-carboxylate (415 mg, 2.16 mmol) and 5-bromo-3-fluorobenzoic acid (365 mg, 1.67 mmol) were converted into 172 mg (26%) of methyl 5-(2-(3-bromo-5-fluorobenzamido)ethyl)thiophene-2-carboxylate.

Step 2. 5-(3-(3',5-Difluoro-[1,1'-biphenyl]-3-ylcarboxamido)propyl)thiophene-2-carboxylic acid In accordance with the procedure of Example 1, step 1, the aryl bromide from step 1 (172 mg, 0.43 mmol) and (3-fluorophenyl)boronic acid (50 mg, 0.36 mmol), were converted into 70 mg (43%) of the title compound after purification employing 3% AcOH/EtOAc.

Example 8

2-Hydroxyethyl 5-(2-(3',4-difluoro-[1,1'-biphenyl]-3-ylcarboxamido)ethyl)thiophene-2-carboxylate Step 1. (Ethyl carbonic) 5-(2-(3',4-difluoro-[1,1'-biphenyl]-3-ylcarboxamido)ethyl)thiophene-2-carboxylic anhydride Triethylamine (56 L, 0.40 mmol) and ethyl chloroformate (19 L, 0.20 mmol) were added sequentially to a solution of 5-(2-(3',4-difluoro-[1,1'-biphenyl]-3-ylcarboxamido)ethyl)thiophene-2-carboxylic acid (71 mg, 0.18 mmol) in $CH_2Cl_2$ (0.95 mL) and DMF (0.95 mL) at 0° C. The mixture was allowed to warm to rt. After 2 h at room temperature, the solution was ready for use in the next step.

Step 2. 2-Hydroxyethyl 5-(2-(3',4-difluoro-[1,1'-biphenyl]-3-ylcarboxamido)ethyl)thiophene-2-carboxylate Ethylene glycol (51 L, 0.91 mmol) was added to one half of the solution of the anhydride solution from step 1 (~0.9 mmol). After stirring 2 days at room temperature, the reaction mixture was concentrated under a stream of nitrogen. The residue was diluted with EtOAc (30 mL) and washed with 1.0 N aqueous HCl (10 mL), $H_2O$ (2×10 mL) and brine (10 mL). The organic phase was dried ($Na_2SO_4$), filtered and concentrated in vacuo. The crude residue was purified by preparative thin layer chromatography (1000 m thickness plate, 10% MeOH/$CH_2Cl_2$) to afford 13 mg (33%) of the title compound.

Example 9

5-(2-(3',4-Difluoro-[1,1'-biphenyl]-3-ylcarboxamido)ethyl)thiophene-2-carboxamide A solution of ammonia (0.23 mL of a 2.0 M solution in methanol, 0.46 mmol) was added to one half of the solution of the anhydride solution from Example 8, step 1 (~0.9 mmol). After stirring overnight at room temperature, the reaction mixture was concentrated in vacuo The residue was diluted with EtOAc (30 mL) and washed with 1.0 N aqueous HCl (10 mL), $H_2O$ (2×10 mL) and brine (10 mL). The organic phase was dried ($Na_2SO_4$), filtered and concentrated in vacuo. The crude residue was purified by preparative thin layer chromatography (500 m thickness plate, 10% MeOH/$CH_2Cl_2$) to afford 8 mg (23%) of the title compound.

Preparation 1

Isopropyl 5-(2-aminoethyl)thiophene-2-carboxylate

Step 1. Isopropyl 5-(2-hydroxyethyl)thiophene-2-carboxylate

A solution of n-butyllithium (37 mL of a 1.6 M solution in hexanes, 59.2 mmol) was added slowly to a solution of tert-butyldimethyl(2-(thiophen-2-yl)ethoxy)silane (see U.S. Pat. No. 5,739,141; 9.5 g, 39.0 mmol) in THF (100 mL) at −78° C. After 1 h at −78° C., isopropyl chloroformate (60 mL of a 1.0 M solution in toluene, 60 mmol) was added slowly. After 1 h at −78° C., the reaction was quenched by addition of saturated aqueous $NH_4Cl$ (150 mL) and was allowed to warm to room temperature. The phases were separated and the organic phase was dried ($Na_2SO_4$), filtered (washing with excess THF) and concentrated in vacuo. The crude residue was dissolved in THF (100 mL), cooled to 0° C. and treated with tetrabutylammonium fluoride (43 mL of a 1.0 M solution in THF, 43 mmol). The reaction was allowed to warm to room temperature and was stirred overnight. The reaction was concentrated in vacuo, saturated aqueous $NH_4Cl$ (100 mL) was added and the mixture was extracted with EtOAc (3×150 mL). The combined extracts were washed with brine (100 mL), dried ($Na_2SO_4$), filtered and concentrated in vacuo. The crude residue was purified on 330 g silica (40% EtOAc/hexanes→60% EtOAc/hexanes, gradient) to afford 6.6 g (71%) of isopropyl 5-(2-hydroxyethyl)thiophene-2-carboxylate.

Step 2. Isopropyl 5-(2-bromoethyl)thiophene-2-carboxylate

Bromine (1.74 mL, 33.9 mmol) was added slowly to a solution of triphenylphosphine (8.9 g, 33.9 mmol) in $CH_2Cl_2$ (65 mL) at −40° C. After 1 h at −40° C., a solution of the alcohol from step 1 (6.6 g, 30.8 mmol) and pyridine (2.5 mL, 30.9 mmol) in $CH_2Cl_2$ (65 mL) was added via cannula. The mixture was allowed to warm to room temperature and was stirred overnight. The reaction was concentrated in vacuo to a brown slurry. The mixture was triturated with hexanes (150 mL) and stirred vigorously. The solids were removed by filtration and the filtrate was concentrated in vacuo to afford 6.2 g (73%) of isopropyl 5-(2-bromoethyl)thiophene-2-carboxylate.

Step 3. Isopropyl 5-(2-azidoethyl)thiophene-2-carboxylate

Sodium azide (697 mg, 10.7 mmol) was added to a solution of the bromide from step 2 (2.7 g, 9.7 mmol) in DMF (39 mL)

at room temperature. After 18 h at room temperature, the reaction mixture was diluted with EtOAc (300 mL) and washed with water (3×100 mL) and brine (50 mL). The organic phases was dried (Na$_2$SO$_4$), filtered and concentrated in vacuo to afford 2.24 g (96%) of isopropyl 5-(2-azidoethyl) thiophene-2-carboxylate.

Step 4. Isopropyl 5-(2-aminoethyl)thiophene-2-carboxylate

Water (0.1 mL) and triphenylphosphine (288 mg, 1.1 mmol) were added sequentially to a solution of the azide from step 3 (239 mg, 1.0 mmol) in THF (2.0 mL) and the reaction was stirred at room temperature overnight. The solvent was removed under a stream of nitrogen and then 1.0 N aqueous HCl (7.5 mL) was added. The mixture was extracted with EtOAc (2×5 mL). The aqueous phase was basified with 2.0 M aqueous NaOH (5 mL). The mixture was extracted with EtOAc (3×10 mL) and these extracts were dried (Na$_2$SO$_4$), filtered and concentrated in vacuo to afford 175 mg (82%) of the title compound.

In Vivo Examples

U.S. Pat. No. 7,091,231 describes the methods used for these in vivo tests.

Isopropyl 5-(2-(3',4-difluoro-[1,1'-biphenyl]-3-ylcarboxamido)ethyl)thiophene-2-carboxylate was tested in normotensive dogs at 0.05%, dosing once daily for 5 days. The maximum intraocular pressure (IOP) decrease from baseline was 5.2 mmHg (32%) at 78 h; the maximum ocular surface hyperemia (OSH) score was 0.8 at 28 h. This compound was also tested in laser-induced hypertensive monkeys, using one single day dose. At 0.05%, the maximum IOP decrease from baseline was 6.9 mmHg (19%) at 6 h.

2-Hydroxyethyl 5-(2-(3',4-difluoro-[1,1'-biphenyl]-3-ylcarboxamido)ethyl)thiophene-2-carboxylate was tested in normotensive dogs at 0.05%, dosing once daily for 5 days. The maximum intraocular pressure (IOP) decrease from baseline was 6.6 mmHg (50%) at 52 h; the maximum ocular surface hyperemia (OSH) score was 1.6 at 54 h. This compound was also tested in laser-induced hypertensive monkeys, using one single day dose. At 0.05%, the maximum IOP decrease from baseline was 13.1 mmHg (31%) at 6 h.

While this invention has been described with respect to these specific examples, it is understood that other modifications and variations are possible without departing from the spirit of the invention.

What is claimed is:

1. A compound having the structure:

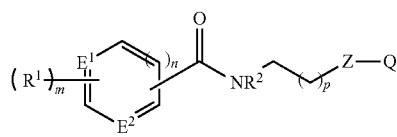

wherein:
$E^1$ and $E^2$ are each independently $CR^1$, O, NH, or N;
Q is $CO_2R^3$, $CH_2OR^3$, $CON(R^3)_2$, or tetrazol-5-yl;
Z is interarylene, n-propyl, $CH_2SCH_2$, or $CH_2OCH_2$;
each $R^1$ is a substituted $C_5$-$C_7$ aryl;
$R^2$ is H or lower alkyl;
$R^3$ is H, lower alkyl, phenyl, biphenyl, $CF_3$, $C(O)R^3$, or $SO_2R^3$;
n is 0 or 1;
m is 1 to 5; and
p is 0 to 5;
or a pharmaceutically acceptable salt, tautomer, enantiomer, or diastereomer thereof.

2. The compound of claim 1 wherein the interarylene is thiophenylene, interfurylene or interthiazolene.

3. The compound of claim 1 wherein $R^1$ is substituted phenyl.

4. The compound of claim 3 the substituted phenyl bears substituents selected from halogen, lower alkyl, lower alkoxy, or $CF_3$.

5. The compound of claim 4 wherein the substituent is halogen.

6. The compound of claim 5 wherein the substituent is fluoro.

7. The compound of claim 1, wherein Q is $CO_2R^3$.

8. The compound of claim 7 wherein $R^3$ is H or lower alkyl.

9. The compound of claim 8 wherein $R^3$ is H.

10. A compound having any one of the following structures:

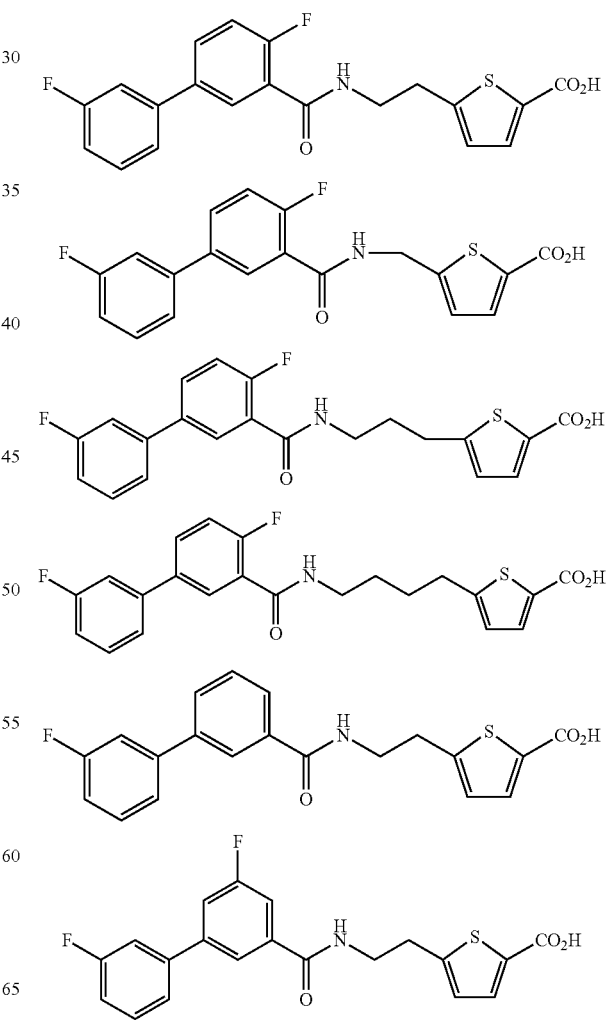

-continued

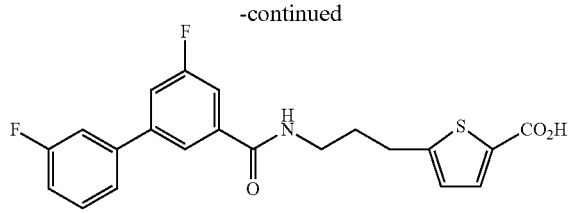

or a pharmaceutically acceptable salt, tautomer, enantiomer, or diastereomer thereof.

11. A compound having the structure:

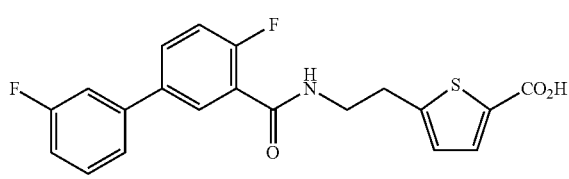 [SMILES: O=C(O)c1ccc(CCNC(=O)c2cc(-c3cccc(F)c3)ccc2F)s1]

or a pharmaceutically acceptable salt, tautomer, enantiomer, or diastereomers thereof.

12. A composition comprising at least one compound according to claim 1, or a pharmaceutically acceptable salt, tautomer, enantiomer, or diastereomer thereof, and at least one pharmaceutically acceptable excipient.

13. A method of treating glaucoma or ocular hypertension comprising administering to a subject in need thereof a compound according to claim 1.

14. The method of claim 13 wherein the subject is human.

15. A kit comprising the composition of claim 12, a container, and instructions for administration of the composition to a subject in need thereof for the treatment of glaucoma or ocular hypertension.

16. A composition comprising at least one compound having the structure:

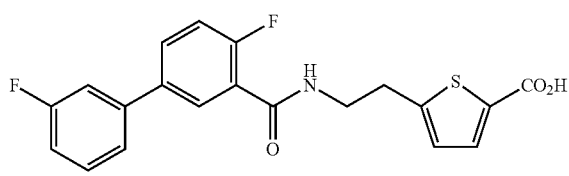 [SMILES: O=C(O)c1ccc(CCNC(=O)c2cc(-c3cccc(F)c3)ccc2F)s1]

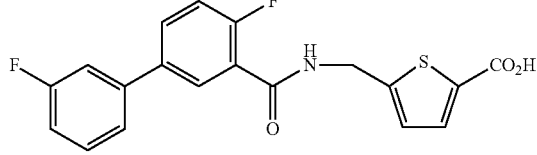

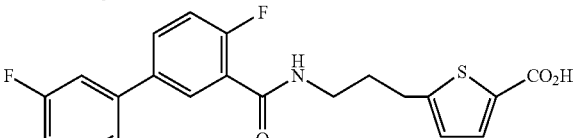

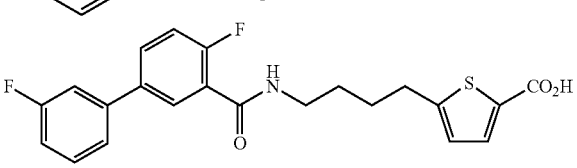

-continued

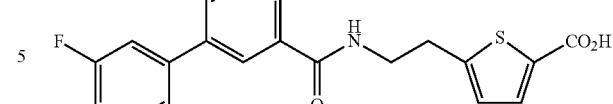

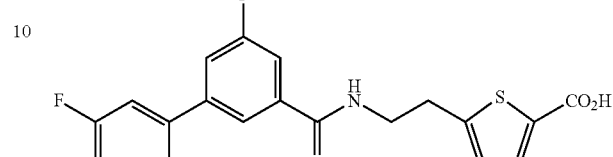

or

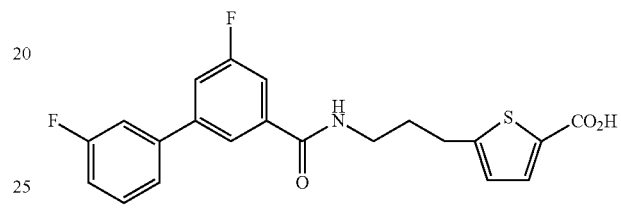

or a pharmaceutically acceptable salt, tautomer, enantiomer, or diastereomer thereof, and at least one pharmaceutically acceptable excipient.

17. A composition comprising at least one compound having the structure:

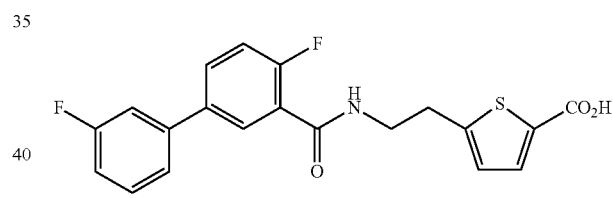

or a pharmaceutically acceptable salt, tautomer, enantiomer, or diastereomer thereof, and at least one pharmaceutically acceptable excipient.

18. A method of treating glaucoma or ocular hypertension comprising administering to a subject in need thereof a compound having the structure:

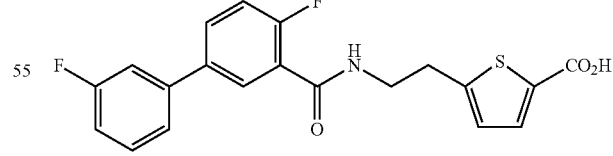

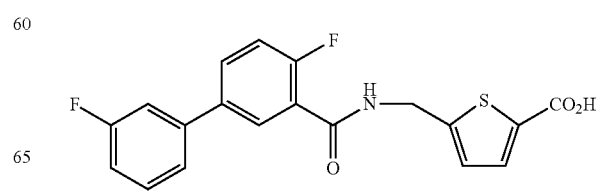

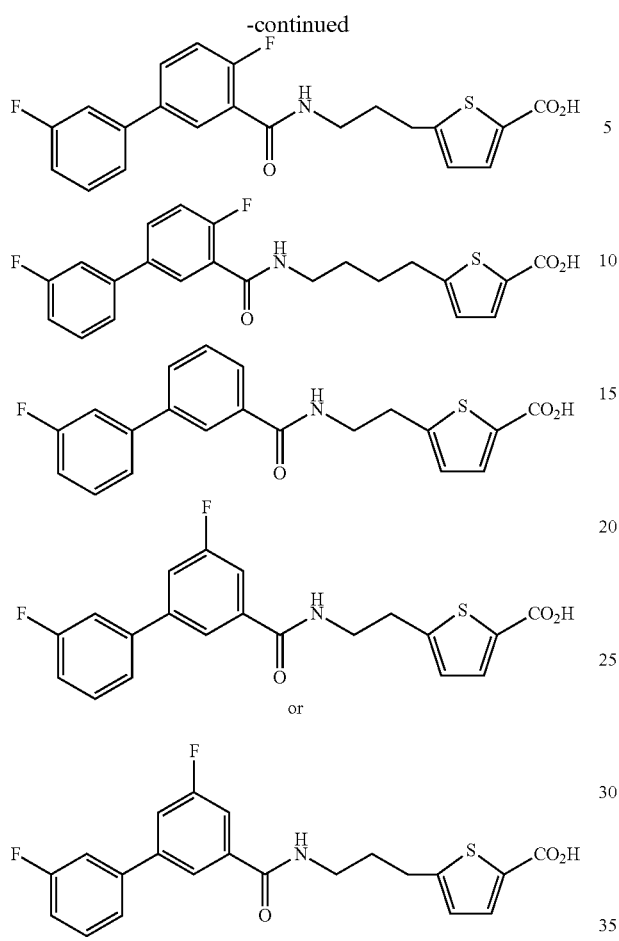

or a pharmaceutically acceptable salt, tautomer, enantiomer, or diastereomer thereof.

19. A method of treating glaucoma or ocular hypertension comprising administering to a subject in need thereof a compound having the structure:

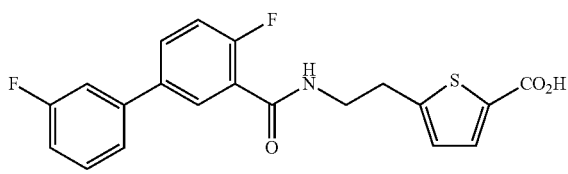 [SMILES: O=C(O)c1ccc(CCNC(=O)c2cc(-c3cccc(F)c3)ccc2F)s1]

or a pharmaceutically acceptable salt, tautomer, enantiomer, or diastereomer thereof.

20. A compound having the structure:

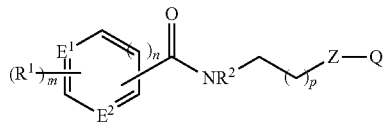

wherein:
  $E^1$ is $CR^1$;
  $E^2$ is H;
  Q is $CO_2R^3$, $CH_2OR^3$, $CON(R^3)_2$, or tetrazol-5-yl;
  Z is interarylene, n-propyl, $CH_2SCH_2$, or $CH_2OCH_2$;
  each $R^1$ is a substituted $C_5$-$C_7$ aryl;
  $R^2$ is H or lower alkyl;
  $R^3$ is H, lower alkyl, phenyl, biphenyl, $CF_3$, $C(O)R^3$, or $SO_2R^3$;
  n is 1;
  m is 1 to 5; and
  p is 0 to 5;
or a pharmaceutically acceptable salt, tautomer, enantiomer, or diastereomer thereof.

21. A composition comprising at least one compound according to claim 20, or a pharmaceutically acceptable salt, tautomer, enantiomer, or diastereomer thereof, and at least one pharmaceutically acceptable excipient.

22. A method of treating glaucoma or ocular hypertension comprising administering to a subject in need thereof a compound according to claim 20.

23. The method of claim 22 wherein the subject is human.

24. A kit comprising the composition of claim 21, a container, and instructions for administration of the composition to a subject in need thereof for the treatment of glaucoma or ocular hypertension.

* * * * *